United States Patent
Ruszkowski et al.

(10) Patent No.: US 12,059,311 B2
(45) Date of Patent: Aug. 13, 2024

(54) SYSTEMS AND METHODS FOR AUTOMATIC GRIP ADJUSTMENT DURING ENERGY DELIVERY

(71) Applicant: INTUITIVE SURGICAL OPERATIONS, INC., Sunnyvale, CA (US)

(72) Inventors: Angelica Ruszkowski, Santa Clara, CA (US); Gabriel F Brisson, Sunnyvale, CA (US); Craig R. Gerbi, Half Moon Bay, CA (US); Jason Hemphill, Los Gatos, CA (US); Mathew Nussbaum, Campbell, CA (US); Harsukhdeep Singh Ratia, Foster City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1002 days.

(21) Appl. No.: 16/970,929

(22) PCT Filed: Feb. 20, 2019

(86) PCT No.: PCT/US2019/018833
§ 371 (c)(1),
(2) Date: Aug. 18, 2020

(87) PCT Pub. No.: WO2019/164995
PCT Pub. Date: Aug. 29, 2019

(65) Prior Publication Data
US 2020/0390512 A1    Dec. 17, 2020

Related U.S. Application Data

(60) Provisional application No. 62/633,289, filed on Feb. 21, 2018.

(51) Int. Cl.
*A61B 18/12*    (2006.01)
*A61B 18/08*    (2006.01)
(Continued)

(52) U.S. Cl.
CPC ............ *A61B 90/03* (2016.02); *A61B 18/085* (2013.01); *A61B 18/1445* (2013.01);
(Continued)

(58) Field of Classification Search
CPC .............. A61B 18/085; A61B 18/1445; A61B 2018/00666; A61B 2018/00678; A61B 2018/00875; A61B 34/35
See application file for complete search history.

(56) References Cited

U.S. PATENT DOCUMENTS 5,431,645 A * 7/1995 Smith ................... A61B 10/06
606/1
8,568,411 B2    10/2013 Falkenstein et al.
(Continued)

FOREIGN PATENT DOCUMENTS

| CN | 101683284 A | 3/2010 |
|---|---|---|
| EP | 1810628 A1 | 7/2007 |

(Continued)

OTHER PUBLICATIONS

International Search Report and Written Opinion for Application No. PCT/US2019/018833, mailed on Jun. 12, 2019, 21 pages (ISRG09500/PCT).

(Continued)

*Primary Examiner* — Daniel W Fowler
(74) *Attorney, Agent, or Firm* — Artegis Law Group, LLP (57) ABSTRACT

Systems and methods for grip adjustment during energy delivery include an instrument comprising an end effector having a first jaw and a second jaw. Each of the first jaw and the second jaw have a corresponding electrode, The systems
(Continued)

and methods further include one or more control units configured to actuate the end effector to grip a material, determine whether a force or torque limit of the actuation is above a first threshold, in response to determining that the force or torque limit is above the first threshold, reduce the force or torque limit, and apply electrical or thermal energy to the material using the electrodes. In some embodiments, the one or more control units are further configured to restore the force or torque limit after application of the electrical or thermal energy to the material is complete. In some embodiments, the force or torque limit is reduced over time.

18 Claims, 3 Drawing Sheets

(51) Int. Cl.
    *A61B 18/14*          (2006.01)
    *A61B 90/00*          (2016.01)
    *A61B 18/00*          (2006.01)

(52) U.S. Cl.
    CPC ............... *A61B 2018/0063* (2013.01); *A61B 2018/00642* (2013.01); *A61B 2018/00678* (2013.01); *A61B 2018/00875* (2013.01); *A61B 2090/031* (2016.02); *A61B 2090/066* (2016.02)

(56) References Cited

U.S. PATENT DOCUMENTS

| | | | |
|---|---|---|---|
| 9,393,017 B2 | 7/2016 | Flanagan et al. | |
| 2003/0158551 A1* | 8/2003 | Paton | A61B 18/1206 606/51 |
| 2006/0058919 A1* | 3/2006 | Sommer | A61B 6/0487 700/245 |
| 2007/0173803 A1* | 7/2007 | Wham | A61B 5/053 606/34 |
| 2008/0046122 A1* | 2/2008 | Manzo | A61B 90/98 700/245 |
| 2008/0172049 A1* | 7/2008 | Bredno | A61B 34/20 606/29 |
| 2010/0076474 A1 | 3/2010 | Yates et al. | |
| 2010/0204695 A1* | 8/2010 | Mehta | A61B 18/1206 606/42 |
| 2011/0015632 A1 | 1/2011 | Artale | |
| 2011/0106141 A1 | 5/2011 | Nakamura | |
| 2011/0118752 A1 | 5/2011 | Itkowitz et al. | |
| 2011/0213357 A1* | 9/2011 | Schechter | A61B 18/1445 606/41 |
| 2012/0209314 A1* | 8/2012 | Weir | A61B 34/37 606/205 |
| 2014/0135762 A1* | 5/2014 | Masuda | A61B 18/1445 606/51 |
| 2014/0136143 A1* | 5/2014 | Stein | A61B 17/00 702/150 |
| 2014/0276738 A1* | 9/2014 | Price | A61B 18/1445 606/33 |
| 2015/0025528 A1* | 1/2015 | Arts | A61B 18/1445 606/46 |
| 2015/0282875 A1 | 10/2015 | Harper et al. | |
| 2016/0074103 A1* | 3/2016 | Sartor | A61B 18/1445 606/51 |
| 2016/0213437 A1 | 7/2016 | Richmond et al. | |
| 2017/0105791 A1 | 4/2017 | Yates et al. | |
| 2017/0156808 A1* | 6/2017 | Auld | A61B 34/70 |
| 2017/0196637 A1 | 7/2017 | Shelton, IV et al. | |
| 2017/0215945 A1 | 8/2017 | Teigan et al. | |
| 2017/0273730 A1* | 9/2017 | Walke | A61B 18/12 |
| 2017/0296257 A1 | 10/2017 | Shelton, IV et al. | |

FOREIGN PATENT DOCUMENTS

| | | |
|---|---|---|
| EP | 2221017 A1 | 8/2010 |
| WO | WO-2012112251 A1 | 8/2012 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP19757910.5, mailed on Nov. 5, 2021, 11 pages.

\* cited by examiner

FIG. 3

SYSTEMS AND METHODS FOR AUTOMATIC GRIP ADJUSTMENT DURING ENERGY DELIVERY

RELATED APPLICATIONS

This application is a U.S. National Stage patent application of International Patent Application No. PCT/US2019/018833, filed on Feb. 20, 2019, the benefit of which is claimed, and claims priority to and benefit of U.S. Provisional Patent Application No. 62/633,289, filed Feb. 21, 2018 and entitled "Systems and Methods for Automatic Grip Adjustment During Energy Delivery," each of which is incorporated by reference herein in its entirety.

TECHNICAL FIELD

Inventive aspects are directed towards the control of end effectors in teleoperated and robotic systems and more specifically to systems and methods for grip adjustment during energy delivery by the end effectors.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, traditional manual surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using teleoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thorascopically, and/or the like) through an opening (e.g., a body wall incision, a natural orifice, and/or the like) to reach a remote surgical site.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept small. One approach to keeping the size of the end effector small is to accomplish actuation of the end effector through the use of one or more inputs at a proximal end of the surgical instrument, where the proximal end is typically located externally to the patient. Various transmission components such as gears, levers, pulleys, cables, rods, belts, bands, and/or the like, may then be used to transmit actions from the one or more inputs along the shaft of the surgical instrument and to actuate the end effector. In the case of a computer-assisted, teleoperational medical device with an appropriate surgical instrument, a transmission mechanism at the proximal end of the instrument interfaces directly, or indirectly through other transmission components, with one or more actuators such as various motors, solenoids, servos, active actuators, hydraulics, pneumatics, and/or the like provided on an articulated arm of the patient side device or a patient side cart. The actuator(s) receive control signals produced in response to user commands provided through a master controller, and provide input to the instrument involving force and/or torque at the proximal end of the transmission mechanism; the various transmission elements ultimately transmit the force or torque to actuate the end effector at the distal end of the transmission mechanism.

The end effectors may also be configured to transmit electrical and/or thermal energy to a gripped material, such as tissue of a patient. The transmitted electrical and/or thermal energy may be used to cauterize, ablate, fuse, seal, etc., and/or combinations thereof, the material, such as prior to cutting the material and/or preparing a portion for excision. Transmission of this electrical and/or thermal energy is often carefully controlled to achieve desired cauterization, ablation, fusing, sealing, and/or the like without undesired side effects.

Minimally-invasive surgery was revolutionized with the advent of computer-assisted surgical systems, such as the da Vinci Surgical System commercialized by Intuitive Surgical. One innovation of the da Vinci Surgical System is the control of end effectors, such as the end effectors of surgical instruments, with high accuracy and high precision to perform desired tasks. As finer and more accurate control of end effectors is desired, it becomes important for control systems to appropriately actuate the end effectors during different procedures, such as during a cauterization, ablation, fusing, sealing, and/or the like procedure.

Accordingly, it would be advantageous to have control systems that are able to appropriately actuate end effectors that are used to perform cauterization, ablation, fusing, sealing, and/or the like procedures.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

Consistent with some embodiments, a system includes an instrument comprising an end effector having a first jaw and a second jaw, each of the first jaw and the second jaw having a corresponding electrode, The system further includes one or more control units configured to actuate the end effector to grip a material, determine whether a force or torque limit of the actuation is above a first threshold, in response to determining that the force or torque limit is above the first threshold, reduce the force or torque limit, and apply electrical or thermal energy to the material using the electrodes.

Consistent with some embodiments, a method of manipulating a material includes actuating one or more of a first jaw and a second jaw of an end effector of an instrument to grip a material, determining, by one or more control units, whether a force or torque limit of the actuation is above a first threshold, in response to determining that the force or torque limit is above the first threshold, reducing, by the one or more control units, the force or torque limit, and applying electrical or thermal energy to the material using electrodes on the jaws.

Consistent with some embodiments, a non-transitory computer-readable medium having stored thereon a plurality of machine-readable instructions which when executed by one or more processors associated with a computer-assisted device are adapted to cause the one or more processors to perform a method. The method includes actuating one or more of a first jaw and a second jaw of an end effector of an instrument to grip a material, determining, by one or more control units, whether a force or torque limit of the actuation is above a first threshold, in response to determining that the force or torque limit is above the first threshold, reducing, by the one or more control units, the force or torque limit, and applying electrical or thermal energy to the material using electrodes on the jaws.

Consistent with some embodiments, a system includes an instrument comprising an end effector having a first jaw and a second jaw, each of the first jaw and the second jaw having a corresponding electrode. The system further includes one or more control units configured to operate one or more of the jaws in a first mode subject to a first force or torque limit, operate one or more of the jaws in a second mode subject to a second force or torque limit higher than the first force or torque limit, grip a material using the jaws, and in response to determining that the one or more of the jaws are being operated in the second mode, switch to operating the one or more of the jaws in the first mode before applying electrical or thermal energy to material using the electrodes.

Consistent with some embodiments, a system includes an instrument including an end effector having a first jaw and a second jaw, each of the first jaw and the second jaw having a corresponding electrode. The system further includes an electrosurgical unit configured to monitor and control application of energy by the electrodes to a material gripped by the jaws and a motion control unit configured to monitor and control actuation of the jaws. The motion control unit is configured to: actuate one or more of the jaws to grip a material based on feedback from the electrosurgical unit, determine whether a force or torque limit of the actuation is above a first threshold, and in response to determining that the force or torque limit is above the first threshold, reduce the force or torque limit.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw).

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

Figure 1:
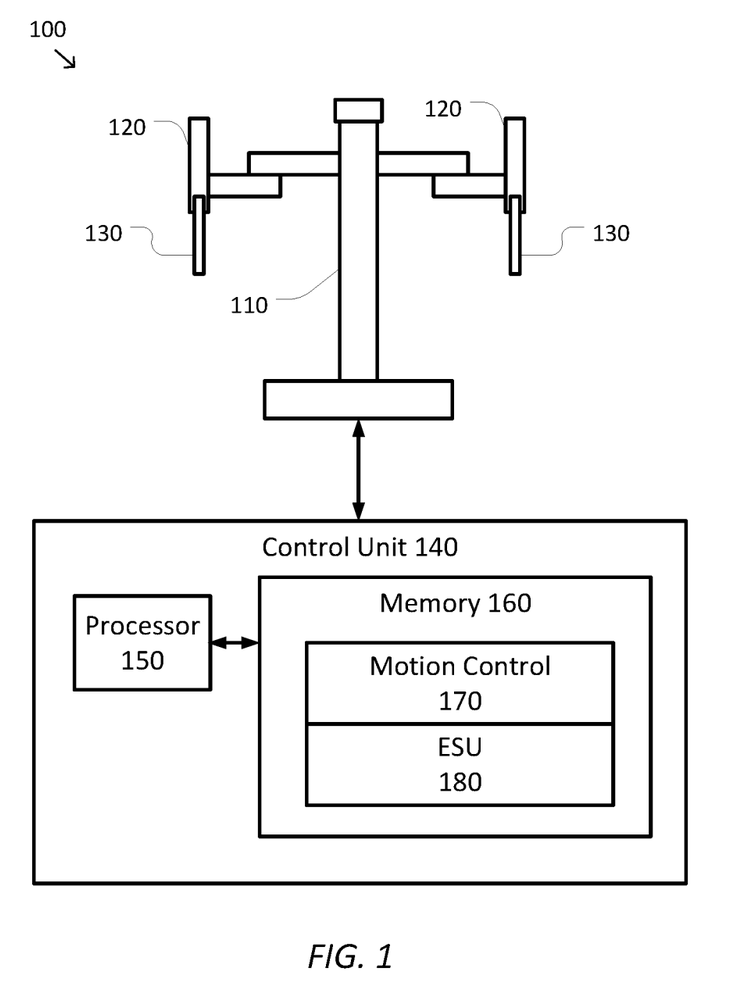
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more articulated or movable arms 120. Each of the one or more moveable arms 120 may support one or more instruments 130. In some examples, computer-assisted device 110 may be consistent with a computer-assisted surgical device. The one or more moveable arms 120 may each provide support for medical instruments 130 such as surgical instruments, imaging devices, and/or the like. Examples of medical instruments 130 include surgical instruments for interacting with tissue, imaging or sensing devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 is coupled to a control unit 140 via an interface. The interface may include one or more wireless links, cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units (CPUs), multi-core processors, microprocessors, microcontrollers, digital signal processors, graphics processing units (GPUs) field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

As shown in FIG. 1, memory 160 includes a motion control module 170 that may be used to support autonomous, semiautonomous, and/or teleoperated control of computer-assisted device 110. Motion control module 170 may include one or more application programming interfaces (APIs) for receiving position, motion, force, torque, and/or other sensor information from computer-assisted device 110, moveable arms 120, and/or instruments 130 and their end effectors, exchanging position, motion, force, torque, and/or collision avoidance information with other control units regarding other devices, and/or planning and/or assisting in the planning of motion for computer-assisted device 110, moveable arms 120, and/or instruments 130. In some examples, motion control module 170 further supports autonomous, semiautonomous, and/or teleoperated control of the instruments 130 and their end effectors during a surgical procedure or other operation.

Memory 160 further includes an electro-surgical unit (ESU) module 180 that may be used to support autonomous, semiautonomous, and/or teleoperated control of an electro-surgical apparatus (not shown) used to cauterize, ablate, fuse, seal, and/or the like a material gripped by one or more end effectors of computer-assisted device 110. ESU module 180 may include one or more application programming interfaces (APIs) for receiving status information regarding voltage, current, impedance, power, phase angle of the power, and/or the like of electrical and/or thermal energy being applied by the electro-surgical apparatus and/or controlling the application of the electrical and/or thermal energy to the gripped material. ESU module 180 may also exchange status and/or control information with motion control module 170 so that control of the computer-assisted device 110 may be adapted based on feedback from the electro-surgical apparatus.

And although motion control module 170 and ESU module 180 are depicted as software applications, motion control module 170 and/or ESU module 180 may optionally be implemented using hardware, software, and/or a combination of hardware and software. In some embodiments, motion control module 170 and ESU module 180 may be included in separate control units, consistent with control unit 140, that are communicatively coupled together.

In some embodiments, computer-assisted system 100 may be found in an operating room and/or an interventional suite. And although computer-assisted system 100 is shown with only one computer-assisted device 110 with two moveable arms 120, one of ordinary skill would understand that computer-assisted system 100 may include any number of devices with moveable arms, end effectors, and/or electro-surgical apparatuses of similar and/or different design from computer-assisted device 110. In some examples, each of the devices may include fewer or more moveable arms, end effectors, and/or electro-surgical apparatuses. In some examples, computer-assisted device 110 may be consistent with a da Vinci Surgical System.

Figure 2:
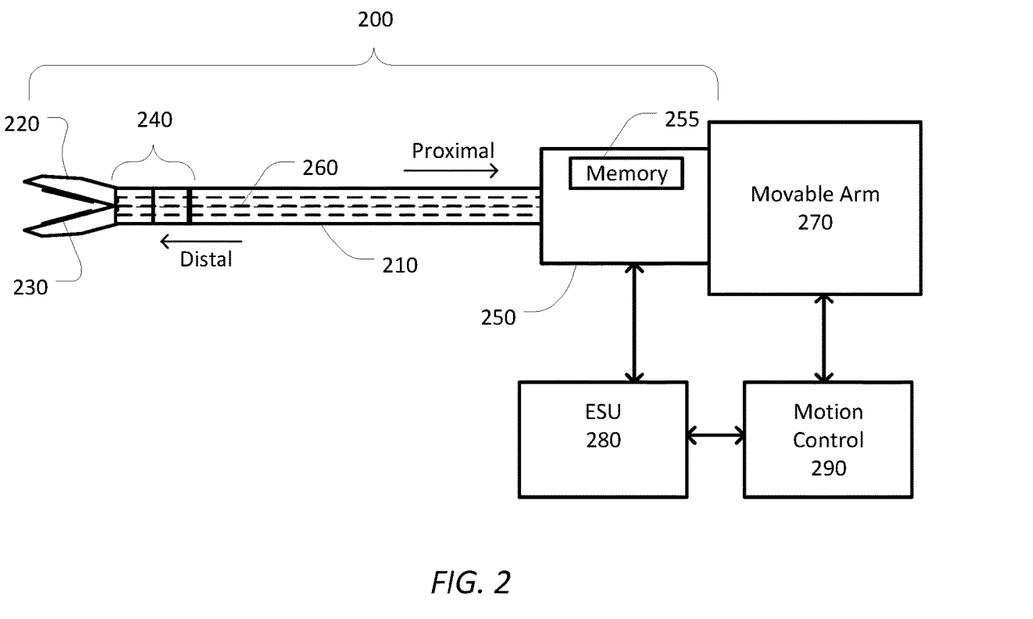
FIG. 2 is a simplified diagram showing an instrument and control apparatus according to some embodiments.

FIG. 2 is a simplified diagram showing an instrument 200 and related control apparatus according to some embodiments. In some embodiments, instrument 200 may be consistent with any of the instruments 130 FIG. 1. The directions "proximal" and "distal" as depicted in FIG. 2 and as used herein help describe the relative orientation and location of components of instrument 200. Distal generally refers to elements in a direction further along a kinematic chain from a user, a base of a computer-assisted device for holding the instrument 200, such as computer-assisted device 110, and/or closest to a work site in the intended operational use of instrument 200. Proximal generally refers to elements in a direction closer along a kinematic chain toward the base of the computer-assisted device, a user or machine holding the instrument 200, and/or one of the moveable arms of the computer-assisted device for holding the instrument 200.

As shown in FIG. 2, instrument 200 includes a long shaft 210 coupling an end effector 220 located at a distal end of shaft 210 to where the instrument 200 is mounted to a moveable arm 270 at a proximal end of instrument 200. Depending upon the particular procedure for which the instrument 200 is being used, shaft 210 may be inserted through an opening in a patient or a work site (e.g., a body wall incision, a natural orifice, an access port, and/or the like) in order to place end effector 220 in proximity to a remote surgical or work site. As further shown in FIG. 2, end effector 220 is generally consistent with a two-jawed gripper-style end effector. The gripping faces of each of the two jaws include a respective electrode 230 for delivering electrical and/or thermal energy to a material gripped by the jaws. Each electrode is electrically and/or thermally isolated from the gripping faces so that the electrical and/or thermal energy is delivered to the gripped material rather than being shorted and/or shunted through the rest of the gripping faces and/or other portions of the jaws and/or end effector 220. In some examples, each electrode 230 may be configured as a mesh, a toothed surface, and/or the like to provide an improved electrical and/or thermal connection with the gripped material by "biting" slightly into the surface of the gripped material. In some embodiments, end effector 220 may further include a cutting mechanism. In some embodiments, end effector 220 and electrodes 230 may correspond to a vessel sealer, an electro-thermal sealing device, an RF bipolar sealing device, and/or the like.

An instrument, such as instrument 200 with end effector 220 typically uses multiple degrees of freedom (DOFs) during its operation. Depending upon the configuration of instrument 200 and the moveable arm 270 and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the work site that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by one or more joints and/or links, such as the joints and links of moveable arm 270, located proximal to shaft 210 and instrument 200. In some examples, an optional articulated wrist 240 may be used to couple end effector 220 to the distal end of shaft 210. In some examples, articulated wrist 240 may optionally include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 further includes a grip DOF used to control the opening and closing of the jaws of end effector 220 and/or an activation DOF used to control the application of electrical and/or thermal energy to a gripped material as is described in further detail below.

Instrument 200 further includes an interface system 250 located at the proximal end of shaft 210. Interface system 250 includes one or more components for introducing forces and/or torques to instrument 200 that can be used to manipulate the various DOFs supported by instrument 200. In some examples, interface system 250 may optionally include one or more motors, solenoids, servos, active actuators, hydraulics, pneumatics, and/or the like that are operated based on signals received from a motion control module 290, which may be consistent with motion control module 170 of control unit 140 of FIG. 1. In some examples, the signals may include one or more currents, voltages, pulse-width modulated wave forms, and/or the like. In some examples, interface system 250 may optionally include one or more shafts, gears, pulleys, rods, bands, and/or the like which may be coupled to corresponding motors, solenoids, servos, active actuators, hydraulics, pneumatics, and/or the like that are part of moveable arm 270. In some examples, the one or more drive inputs, such as shafts, gears, pulleys, rods, bands, and/or the like, are used to receive forces and/or torques from the motors, solenoids, servos, active actuators, hydraulics, pneumatics, and/or the like and apply those forces and/or torques to adjust the various DOFs of instrument 200. In this discussion, both "force" and "torque" are sometimes used individually to indicate linear force, rotational torque, and/or both, as applicable.

Interface system 250 further includes one or more components for interfacing with electrodes 230 and an ESU module 280, which may be consistent with ESU module 180 of control unit 140 of FIG. 1. The one or more components may include components for exchanging signals between electrodes 230 and ESU module 280. In some examples, the signals may include one or more currents, voltages, pulse-width modulated wave forms, and/or the like for transmitting electrical and/or thermal energy to electrodes 230 as directed by ESU module 280. In some examples, the signals may include sensory signals for monitoring the electrical and/or thermal energy delivered by electrodes 230 to gripped material and may include signals for one or more of voltage, current, impedance, power, phase angle of the power, and/or the like.

Interface system 250 further includes a memory 255. Memory 255 is used to store one or more of identification, status, and/or calibration information for instrument 200 and/or end effector 220. In some examples, the identification information may include one or more of a serial number, a model number, a type, and/or the like of instrument 200 and/or end effector 220. In some examples, the status information may include one or more of lifetime, usage counts, energy delivered, and/or the like. In some examples, the calibration information may include one or more of force thresholds, torque thresholds, gains, sensitivities, and/or the like that may be used to customize the operation and/or control of instrument 200 and/or end effector 220 to account for variations in parameters of each individual instrument 200 and/or end effector 220, wear and/or drift over a lifetime of each individual instrument 200 and/or end effector 220, and/or the like.

In some embodiments, the forces and/or torques generated by and/or received by interface system 250 are transferred from interface system 250 and along shaft 210 to the various joints and/or elements of instrument 200 located distal to interface system 250 using one or more drive mechanisms and/or cables 260. In some examples, the one or more drive mechanisms and/or cables 260 may optionally include one or more gears, levers, pulleys, mechanical cables, rods, bands, wires, electrical cables, optical fibers, and/or the like. In some examples, shaft 210 is hollow and the drive mechanisms and/or cables 260 pass along the inside of shaft 210 from interface system 250 to the corresponding DOFs in end effector 220 and/or articulated wrist 240 and/or electrodes 230. In some examples, each of the drive mechanisms may optionally be a mechanical cable disposed inside a hollow sheath or lumen in a Bowden cable like configuration. In some examples, the mechanical cable and/or the inside of the lumen may optionally be coated with a low-friction coating such as polytetrafluoroethylene (PTFE) and/or the like. In some examples, as the proximal end of each of the mechanical cables is pulled and/or pushed inside interface system 250, such as by wrapping and/or unwrapping the cable about a capstan or shaft, the distal end of the cable moves accordingly and applies a suitable force and/or torque to adjust one or more of the DOFs of end effector 220, articulated wrist 240, and/or instrument 200.

According to some embodiments, the ability of electrodes 230 to properly cauterize, ablate, fuse, and/or seal a material gripped by the jaws of end effector 220 may depend on one or more of the geometry of how the jaws grip the material, a level of force and/or torque applied by the jaws to the gripped material, and/or the like. In some examples, when the grip force or torque is too low, insufficient contact is maintained between electrodes 230 and the gripped material to allow for adequate electrical or thermal energy transfer to the material. In some examples, when the grip force or torque is too high, the grip can result in one or more of shorting between electrodes 230, seizing between the gripped material and electrodes 230 where the gripped material sticks to electrodes 230 and/or "glues" electrodes 230 together, poor energy transfer caused by too much desiccation of the material that adversely affects an impedance of the material and/or causes too little of the material to receive energy from electrodes 230, causes undesirable and possibly damaging flex or splay in the jaws, and/or the like. In some examples, when end effector 220 is being operated in a strong grip mode, the resulting grip forces and torques may be too high to allow for proper cauterization, ablation, fusing, sealing, and/or the like to take place. Accordingly, it would be advantageous for ESU module 280 and/or motion control module 290 to monitor the cauterization, ablation, fusing, sealing, and/or the like as it is being performed using electrodes 230 and to adjust the forces and/or torques being applied by the jaws of end effector 220 to improve the likelihood of successful cauterization, ablation, fusing, sealing, and/or the like.

Figure 3:
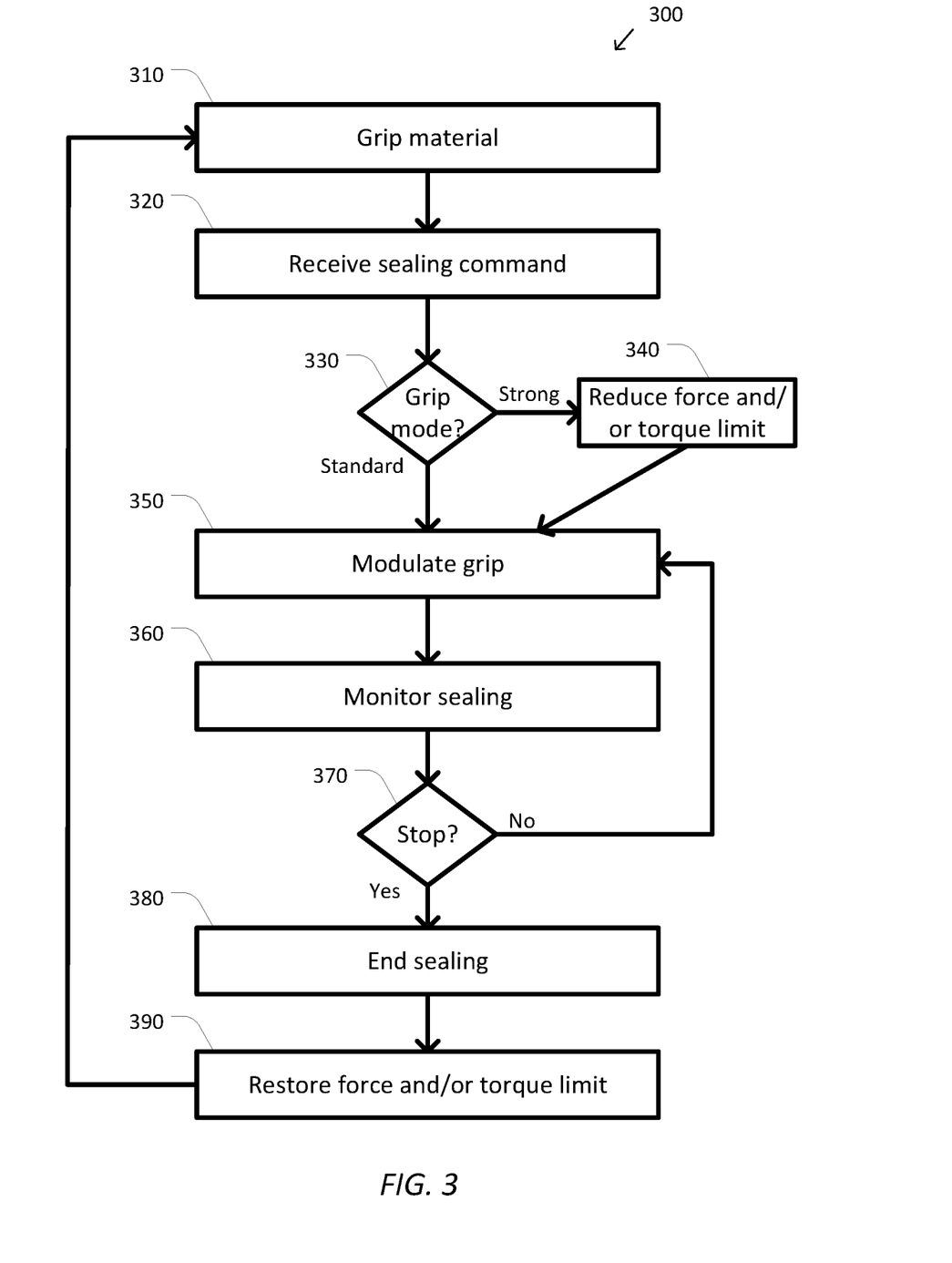
FIG. 3 is a simplified diagram of a method for sealing a material according to some embodiments.

FIG. 3 is a simplified diagram of a method 300 for sealing a material according to some embodiments. One or more of the processes 310-390 of method 300 may be implemented, at least in part, in the form of executable code stored on non-transitory, tangible, machine readable media. This executable code, when run by one or more processors (e.g., the processor 150 in control unit 140), may cause the one or more processors to perform one or more of the processes 310-390. In some embodiments, method 300 may be performed by one or more modules, such as motion control module 170 and/or 290 and/or ESU module 180 and/or 280. In some embodiments, method 300 may be used to concurrently control the actuation of gripping jaws of an end effector, such as end effector 220, and electrodes for delivering electrical and/or thermal energy, such as electrodes 230. In some embodiments, the order of processes of method 300 may occur in a different order than those implied by the flow chart of FIG. 3. In some examples, processes 350-370 may be performed concurrently and/or process 340 may be performed gradually while one or more of processes 350-370 are being performed. According to some embodiments, one or more of processes 350 and/or 390 are optional and may be omitted. And although method 300 is described within the context of sealing, one of ordinary skill would understand that it is also applicable and/or adaptable to other applications of energy delivery involving electrical, thermal, and/or similar energies. In some examples, the other applications of energy delivery include cauterizing, ablating, fusing, and/or the like.

At a process 310, a material is gripped. An end effector, such as end effector 220, is actuated so that the jaws are closed on to the material, preferably to obtain a good broad grip of the tissue that places electrodes, such as electrodes 230, in solid contact with the material where a seal is to be formed. In some examples, the end effector may be actuated by sending one or more control signals to an actuator, such as an actuator coupled to interface system 250, which closes the jaws. A drive mechanism, such as one of the drive mechanisms in shaft 210, may then transfer the actuation of the actuator to a DOF in the end effector. In some examples, the actuation may be performed subject to a force or torque limit that controls the maximum force or torque that may be applied by the jaws to the gripped material. In some examples, the force or torque limit may be calibrated to the end effector and may optionally be stored in a memory, such as memory 255, in the end effector of the corresponding instrument. In some examples, the force or torque limit may be based on one or more of a geometry of the grip, a tooth profile of the electrodes, a pattern and/or angle of a mesh of the electrodes, a length of the jaws, a thermal capacity of the jaws, a stiffness of the jaws, a surface area of the jaws and/or electrodes, and/or the like. In some examples, the force or torque limit may vary based on one or more of an operating mode of the end effector, a type of the end effector, a type of procedure being performed, a type of material being gripped, operator preference, and/or the like. In some examples, the operating mode may be selected from a standard grip mode and a strong grip mode, with the selection being made based on one or more of a command from the operator, a type of procedure being performed, a type of material being gripped, and/or the like.

In some examples, the standard grip mode may include grip forces in a range between 6 and 10 Newtons and the strong grip may include grip forces in a range from 10 to 17 Newtons. In some examples, the standard grip mode may include grip torques in a range between 0.10 and 0.19 Newton-meters and the strong grip mode may include grip torques in a range between 0.19 to 0.38 Newton-meters. In some examples, the force or torque limit may be implemented as a current limit on an actuator, such as a motor. In some examples, the command to grip the material may be received from a master input control being manipulated by an operator, such as a surgeon.

At a process 320, a sealing command is received. In some examples, the sealing command may be received from the operator based on an input received from a switch, button, pedal, and/or similar input device, a voice command, and/or the like. In some examples, once the sealing command is received, an ESU module, such as ESU module 180 and/or 280, may cause the transfer of electrical and/or thermal energy to the tissue gripped during process 310 to occur. In some examples, the energy transfer may be controlled by controlling a voltage between the sealing electrodes (e.g., electrodes 230), a current applied to the sealing electrodes, and/or both. In some examples, the voltage and/or current may be an AC voltage and/or current. In some examples, the voltage may range from 5 to 135 Volts RMS and/or the current may range from 0.5 to 1.75 Amperes RMS. In some examples, a notification may be sent to the operator in the form an audio and/or visual message, haptic feedback, and/or the like indicating the start of sealing.

At a process 330, a grip mode for the end effector is determined. In some examples, the grip mode may be determined based on an operational mode setting commanded by the operator, the motion control module, and/or the like. In some examples, the grip mode may be determined based on a force and/or torque by which the jaws are gripping the material. In some examples, the force and/or torque of the gripping may be determined based on one or more of a current in one or more actuators actuating the jaws, a force and/or torque sensor, and/or the like. The force and/or torque of the gripping is then compared to one or more force and/or torque thresholds that classify the force and/or torque of the gripping as within a range of standard forces and/or torques or within a range of strong forces and/or torques. In some examples, the one or more force and/or torque thresholds are calibrated to the end effector and may be stored in a memory, such as memory 255, in the end effector of the corresponding instrument. In some examples, the one or more force and/or torque thresholds may be based on one or more of a geometry of the grip, a tooth profile of the sealing electrodes, a pattern and/or angle of a mesh of the sealing electrodes, a length of the jaws, a thermal capacity of the jaws, a stiffness of the jaws, a surface area of the jaws and/or sealing electrodes, and/or the like. In some examples, the one or more force and/or torque thresholds may vary based on one or more of an operating mode of the end effector, a type of the end effector, a type of procedure being performed, a type of material being gripped, operator preference, and/or the like. In some examples, the force and/or torque thresholds may be approximately 10 Newtons and 0.19 Newton-meters, respectively. When the grip mode is the strong grip mode, a force or torque limit is reduced using a process 340. When the grip mode is the standard grip mode, sealing started during process 320 continues with a process 350.

At the process 340, a force and/or torque limit for the end effector is reduced. Because an excessive grip force and/or torque during sealing may result in poor sealing, the force and/or torque limit of the control algorithm actuating the jaws of the end effector is reduced to improve the likelihood of good sealing. In some examples, a reduction in the force and/or torque limit may result in a corresponding decrease in the actual force and/or torque being applied by the jaws to the material and/or limits the ability of the operator to command the jaws to grip the material with greater force and/or torque than the reduced force and/or torque limit. In some examples, the force and/or torque limit is reduced to an upper limit or just below the upper limit for the standard grip mode. In some examples, the force limit is reduced to approximately 9 Newtons or 10 Newtons and/or the torque limit is reduced to approximately 0.17 Newton-meters or 0.19 Newton-meters. In some examples, the force and/or torque limit is reduced gradually over time to avoid any abrupt changes in the actual force and/or torque of the grip, poor or undesirable end effector behavior, and/or the like. In some examples, the force and/or torque limit is reduced monotonically. In some examples, the force and/or torque limit is reduced according to a function, such as a step, a series of steps, a ramp, a sigmoid ("s"-shaped) curve, an exponential drop, a parabolic drop, and/or the like. In some examples, a notification may be sent to the operator in the form an audio and/or visual message, haptic feedback, and/or the like indicating the reduction of the force and/or torque limit. While the force and/or torque limit is being reduced the sealing started during process 320 continues. Once the force and/or torque limit is reduced, method 300 continues with process 360.

At the optional process 350, the grip is modulated. In some examples, the likelihood of the undesirable effects of shorting, seizing, poor energy transfer, and/or the like may also be reduced by modulating the grip. In some examples, the modulation may include one or more of modulating an angle of the jaws (e.g., modulating the opening and closing of the jaws), modulating a position of the jaws (e.g., modulating one or more of the jaws to move side-to-side and/or forward-to-back), modulating the force and/or torque limit, and/or the like. In some examples, the modulation occurs at a frequency that is higher than could be performed manually by the operator, such as a frequency in a range of 0.5 to 5 Hertz. In some examples, the modulation may occur according to a periodic function such as a sinusoid, square wave, triangular wave, and/or the like. In some examples, the modulation may continue throughout the sealing.

At a process 360, the sealing is monitored by, for example, the ESU module. In some examples, the sealing is monitored to determine whether the sealing is following an expected sealing profile, whether problems (e.g., shorting between the sealing electrodes is detected), completion of the sealing, and/or the like. In some examples, the sealing may be monitored based on tracking one or more of a voltage between the sealing electrodes, a current applied to the sealing electrodes, a power level of the electrical and/or thermal energy being delivered by the sealing electrodes, a phase angle/power factor of the power being delivered by the sealing electrodes, an impedance of the gripped tissue (e.g., as determined based on the voltage and current), and/or the like.

Figure 4:
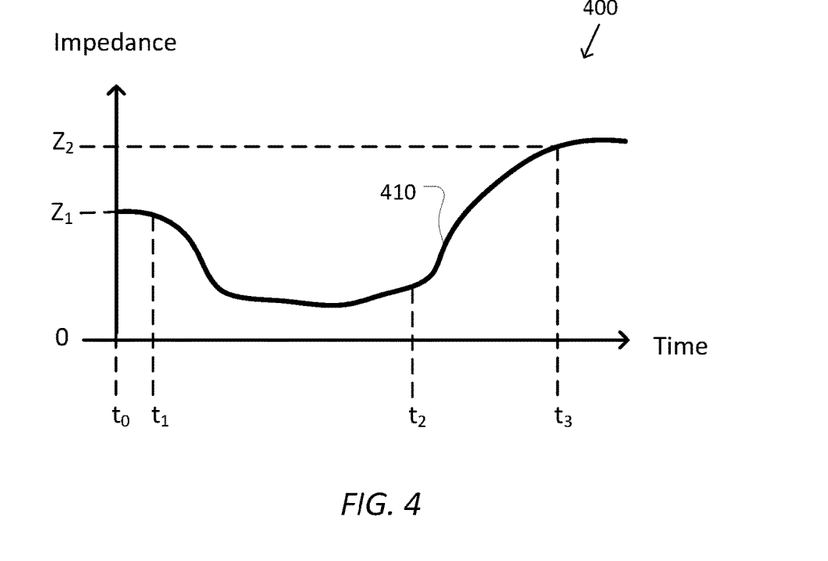
FIG. 4 is a simplified diagram of changes in a property of a material during a sealing procedure according to some embodiments.

FIG. 4 is a simplified diagram 400 of changes in a property of a material during a sealing procedure according to some embodiments. As shown in FIG. 4, changes in an impedance of a gripped material, such as anatomical tissue, are shown during an exemplary sealing procedure. In some examples, the impedance of the gripped material may be determined based on the voltage and current being applied to the gripped material by the sealing electrodes. The impedance profile during sealing of anatomical tissue (e.g., a blood vessel) often follows a fairly predictable curve, such as the impedance cure 410 shown in FIG. 4. Upon gripping of the tissue and starting of the sealing process at a time to, an initial impedance ($Z_1$) of the tissue is observed. As the tissue is heated by the sealing and desiccation occurs, the impedance begins to drop as indicated at time $t_1$. The impedance then remains relatively steady as further sealing occurs until, at a time $t_2$, the impedance begins to rise as further desiccation and sealing reduce fluids in the tissue. At time $t_3$, the impedance then reaches a threshold impedance ($Z_2$) at which the impedance begins to level off and sealing is considered complete. In some examples, $Z_2$ may be in a range from 200 to 300 ohms. In some examples, the threshold impedance $Z_2$ may be set based on a type of tissue being sealed, a model and/or type of the end effector performing the sealing, and/or the like. Additional details regarding sealing profiles may be found in U.S. Pat. App. Pub. No. 2011/0319882 (disclosing "Low Power Tissue Sealing Device and Methods"), which is hereby incorporated by reference in its entirety.

Referring back to FIG. 3, at a process 370, it is determined whether a stopping condition is detected. In some examples, the stopping condition may correspond to an operator providing a command to terminate the sealing procedure. In some examples, the stopping condition may correspond to detecting successful completion of the sealing procedure. In some examples, the successful completion may correspond to an impedance of the material being sealed reaching a threshold impedance (e.g., $Z_2$), detection of the impedance of the material leveling off after rising, a configurable time limit (e.g., 0.5 to 3.5 seconds), determining that a total energy delivered to the material by the sealing electrodes has reached and/or exceeded a configurable threshold energy level (e.g., 10-50 Joules), and/or the like. In some examples, one or more of the threshold impedance, time limit, and/or the threshold energy level may be based on a material being sealed, a model and/or type of end effector performing the sealing, a procedure being performed, operator preference, and/or the like. In some examples, the stopping condition may correspond to detecting one or more undesirable measures of the sealing that may be indicative of shorting, seizing, poor seal formation, and/or the like. In some examples, the undesirable measures may include one or more of an impedance of the material falling below a configurable minimum impedance threshold, a change in impedance (e.g., a rate of change and/or derivative of the impedance of approximately −750 ohms/second or more) falling below a configurable negative change in impedance threshold, detecting that a phase angle of the power being delivered by the sealing electrodes is above a phase angle threshold (e.g., approximately 75 degrees, indicating that high current through the material and low impedance of the material is being observed), and/or the like. In some examples, one or more of the minimum impedance threshold, the negative change in impedance threshold, and/or the phase angle threshold may be based on a material being sealed, a model and/or type of end effector performing the sealing, a procedure being performed, operator preference, and/or the like. When a stopping condition is not detected, sealing continues by returning to process 350. When a stopping condition is detected, the sealing procedure ends beginning with a process 380.

At the process 380, the sealing procedure is ended by removing the voltage and/or current being applied to the sealing electrodes so that additional electrical and/or thermal energy is no longer being transferred to the material by the sealing electrodes. In some examples, a notification may be sent to the operator in the form an audio and/or visual message, haptic feedback, and/or the like indicating the sealing procedure is being stopped and/or the reasons for ending the sealing procedure (e.g., by command, successful completion, detection of an undesirable measure, and/or the like).

At an optional process 390, the force and/or torque limit is returned to its pre-sealing level when process 340 was used to reduce the force and/or torque limit. In some examples, the force and/or torque limit is gradually restored (e.g., increased) over time to avoid any abrupt changes in the actual force and/or torque of the grip, poor or undesirable end effector behavior, and/or the like. In some examples, the force and/or torque limit is restored monotonically. In some examples, the force and/or torque limit is restored according to a function, such as a step, a series of steps, a ramp, a sigmoid ("s"-shaped) curve, an exponential rise, a parabolic rise, and/or the like. In some examples, a notification may be sent to the operator in the form an audio and/or visual message, haptic feedback, and/or the like indicating the restoring of the force and/or torque limit.

As discussed above and further emphasized here, FIG. 3 is merely an example which should not unduly limit the scope of the claims. One of ordinary skill in the art would recognize many variations, alternatives, and modifications. In some embodiments, the detection of undesirable measures associated with the sealing during process 370 may not initially result in ending of the sealing procedure. In some examples, instead of ending the sealing procedure when undesirable measures are detected, the level of modulation being performed by process 350 may be increased for a configurable period of time to see if the increase in modulation is able to mitigate the cause of the undesirable measures before ending the sealing procedure at the end of the configurable period of time when suitable mitigation is not obtained. In some examples, the configurable period of time may be in a range of approximately 1 to 2 seconds. In some examples, the configurable period of time may be based one or more of an operating mode of the end effector, a type of the end effector, a type of procedure being performed, a type of material being sealed, operator preference, and/or the like. In some examples, a notification may be sent to the operator in the form an audio and/or visual message, haptic feedback, and/or the like indicating the increase in modulation.

According to some embodiments, three or more grip modes (e.g., more than strong and standard) are possible. In some examples, when a grip mode other than the standard grip mode is determined during process 330 the force or torque limit may be reduced using process 340. In some examples, when a grip mode with a grip force or torque that is too low to support sealing is detected during process 330, the force or torque limit may be increased. In some examples, when a grip mode where the force and/or torque by which the jaws are gripping the material is within an acceptable range is detected during process 330, the force or torque limit may remain unchanged.

According to some embodiments, sealing may not begin right after receiving the sealing command during process 320. In some examples, processes 330 and/or 340 may complete before the sealing electrodes are energized and electrical and/or thermal energy is transferred to the gripped material.

According to some embodiments, method 300 is not performed when a desired grip position cannot be reached during process 310 subject to the force and/or torque limit for the end effector. In some examples, a notification may be sent to the operator in the form an audio and/or visual message, haptic feedback, and/or the like indicating the inability to reach the desired grip position and thus the inadvisability of performing the sealing procedure. In some examples, the operator may override the inability to reach the desired grip position and proceed with the sealing procedure from the current grip position.

Some examples of control units, such as control unit 140 may include non-transitory, tangible, machine readable media that include executable code that when run by one or more processors (e.g., processor 150) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system comprising:
an instrument comprising an end effector having a first jaw and a second jaw, each of the first jaw and the second jaw having a corresponding electrode; and
one or more control units configured to:
actuate the end effector to grip a material, and
in response to receiving a command to apply electrical or thermal energy to the material:
determine whether a force or torque limit of the actuation is above a first threshold that corresponds to a force or torque that separates a first range of forces or torques of a first gripping mode and a second range of forces or torques of a second gripping mode;
in response to determining that the force or torque limit is above the first threshold, reduce the force or torque limit; and
apply electrical or thermal energy to the material using the electrodes.

2. The system of claim 1, wherein the first threshold is stored in a memory of the instrument.

3. The system of claim 1, wherein the first threshold is based on one or more of a type of the instrument, a model of the instrument, a procedure being performed, a type of the material, or a preference of an operator.

4. The system of claim 1, wherein the force or torque limit is reduced monotonically over time.

5. The system of claim 1, wherein the instrument is a vessel sealer, an electro-thermal sealing device, or an RF bipolar sealing device.

6. The system of claim 1, wherein the one or more control units are further configured to:
detect a stopping condition; and
end the application of electrical or thermal energy to the material in response to detecting the stopping condition;
wherein:
the stopping condition is a stop command from an operator or corresponds to a completion of sealing of the material; and
to detect the completion of the sealing, the one or more control units are configured to detect one or more of an increase in an impedance of the material above an impedance threshold, a leveling off of the impedance after a rise in the impedance, an elapsed time, or an amount of energy transferred to the material exceeding an energy threshold.

7. The system of claim 6, wherein:
the one or more control units are configured to monitor the application of the electrical or thermal energy to the material;
the stopping condition corresponds to detection of an undesirable condition based on the monitoring; and
to detect the undesirable condition, the one or more control units are configured to detect one or more of the impedance of the material falling below a second impedance threshold, a change in the impedance falling below a change in impedance threshold, or a phase angle of power delivered to the material by the electrodes exceeding a phase angle threshold.

8. The system of claim 1, wherein the one or more control units are further configured to restore the force or torque limit after application of the electrical or thermal energy to the material is complete.

9. The system of claim 1, wherein the one or more control units are further configured to modulate the gripping of the material by modulating one or more of an angle between the jaws, a position of one of the jaws relative to another of the jaws, or the force or torque limit.

10. The system of claim 1, wherein the one or more control units are further configured to:
operate one or more of the jaws in the first gripping mode subject to the force or torque limit of the actuation; and
in response to determining that the force or torque limit is above the first threshold, switch to operating the one or more of the jaws in the second gripping mode.

11. A method of manipulating a material, the method comprising:
actuating one or more of a first jaw and a second jaw of an end effector of an instrument to grip a material;
in response to receiving a command to apply electrical or thermal energy to the material:
determining, by one or more control units, whether a force or torque limit of the actuation is above a first threshold that corresponds to a force or torque that separates a first range of forces or torques of a first gripping mode and a second range of forces or torques of a second gripping mode;

in response to determining that the force or torque limit is above the first threshold, reducing, by the one or more control units, the force or torque limit; and applying electrical or thermal energy to the material using electrodes on the jaws.

12. The method of claim 11, further comprising:

detecting a stopping condition; and ending the application of electrical or thermal energy to the material in response to detecting the stopping condition;

wherein:

the stopping condition is a stop command from an operator or corresponds to a completion of sealing of the material; and detecting the completion of the sealing comprises detecting one or more of an increase in an impedance of the material above an impedance threshold, a leveling off of the impedance after a rise in the impedance, an elapsed time, or an amount of energy transferred to the material exceeding an energy threshold.

13. The method of claim 11, further comprising modulating the gripping of the material by modulating one or more of an angle between the jaws, a position of one of the jaws relative to another of the jaws, or the force or torque limit.

14. The method of claim 13, further comprising:

operating, by the one or more control units, one or more of the jaws in the first gripping mode subject to the force or torque limit of the actuation; and in response to determining that the force or torque limit is above the first threshold, switching to operating the one or more of the jaws in the second gripping mode.

15. The method of claim 11, further comprising determining the force or torque limit based on one or more of a geometry by which the material is gripped, a tooth profile of the electrodes, a pattern of the electrodes, an angle of a mesh of the electrodes, a length of the first and second jaws, a thermal capacity of the first and second jaws, a stiffness of the first and second jaws, a surface area of the first and second jaws, or a surface area of the electrodes.

16. A non-transitory computer-readable medium having stored thereon a plurality of machine-readable instructions which when executed by one or more processors associated with a computer-assisted device are adapted to cause the one or more processors to perform a method comprising:

actuating one or more of a first jaw and a second jaw of an end effector of an instrument to grip a material located between the first jaw and the second jaw;

in response to receiving a command to apply electrical or thermal energy to the material:

determining, by one or more control units, whether a force or torque limit of the actuation is above a first threshold that corresponds to a force or torque that separates a first range of forces or torques of a first gripping mode and a second range of forces or torques of a second gripping mode;

in response to determining that the force or torque limit is above the first threshold, reducing, by the one or more control units, the force or torque limit; and applying electrical or thermal energy to the material using electrodes on the jaws.

17. The non-transitory computer-readable medium of claim 16, wherein the method further comprises:

detecting a stopping condition; and ending the application of electrical or thermal energy to the material in response to detecting the stopping condition;

wherein:

the stopping condition is a stop command from an operator or corresponds to a completion of sealing of the material; and detecting the completion of the sealing comprises detecting one or more of an increase in an impedance of the material above an impedance threshold, a leveling off of the impedance after a rise in the impedance, an elapsed time, or an amount of energy transferred to the material exceeding an energy threshold.

18. The non-transitory computer-readable medium of claim 16, wherein the method further comprises modulating the gripping of the material by modulating one or more of an angle between the jaws, a position of one of the jaws relative to another of the jaws, or the force or torque limit.

* * * * *